United States Patent [19]

Schoeffel et al.

[11] 4,088,407
[45] May 9, 1978

[54] HIGH PRESSURE FLUORESCENCE FLOW-THROUGH CUVETTE

[75] Inventors: Dietmar M. Schoeffel; Armin K. Sonnenschein, both of Hillsdale, N.J.

[73] Assignee: Schoeffel Instrument Corp., Westwood, N.J.

[21] Appl. No.: 703,788

[22] Filed: Jul. 9, 1976

Related U.S. Application Data

[63] Continuation-in-part of Ser. No. 450,676, Mar. 13, 1974, Pat. No. 3,985,441.

[51] Int. Cl.² .................... G01N 1/10; G01N 21/52
[52] U.S. Cl. .................................. 356/85; 250/576; 356/246
[58] Field of Search .................. 356/85, 75, 103, 104, 356/244, 181, 246; 250/574, 576

[56] References Cited

U.S. PATENT DOCUMENTS

| | | | |
|---|---|---|---|
| 3,508,830 | 4/1970 | Hopkins et al. | 356/103 |
| 3,564,263 | 2/1971 | Shaw | 356/103 X |
| 3,705,771 | 12/1972 | Friedman | 250/576 X |
| 3,849,654 | 11/1974 | Malvin | 356/75 X |

*Primary Examiner*—F. L. Evans
*Attorney, Agent, or Firm*—Samuelson & Jacob

[57] ABSTRACT

A cuvette for liquid chromatographic analysis and like determinations having a chamber through which the liquid being analyzed flows, a single optical body for directing exciting light to the chamber and emitted light to a detector and means for holding the optical body in initmate contact with the chamber.

13 Claims, 5 Drawing Figures

HIGH PRESSURE FLUORESCENCE FLOW-THROUGH CUVETTE

This application is a continuation-in-part of application Ser. No. 450,676, filed Mar. 13, 1974, now U.S. Pat. No. 3,985,441.

The invention relates to cuvettes which are used to contain the liquid which is to be subjected to liquid chromatographic analysis. More particularly, the invention is directed toward providing cuvettes which may be used for the analysis of the fluorescing characteristics of the liquid under study as well as for the measurement of the liquid's transmission characteristics and optical density.

The measurement of fluorescence in the minute quantities encountered in flowing media in cuvettes such as, for instance, in high pressure, liquid chromatography has become an increasing problem. The liquid flow emerging from either high or low pressure chromatographic columns is usually channeled through extremely narrow tubing with inside diameters of the order of from five to twenty thousandths of an inch. This flowing liquid consists of a solvent in which certain separated compounds are carried in confined sections. These sections of compounds, whose concentration and optical density are of interest to the investigator, very often have fluorescent properties. Investigation of the fluorescing of the compounds by means of a suitable detector is frequently very desirable.

The detectors heretofore available have suffered because there was insufficient signal yield. This low yield resulted because there was insufficient interception of the fluorescent energy. To overcome this disadvantage, more and more sensitive photomultipliers have been used. However, the increase in the sensitivity of the photomultipliers has introduced an increase in background noise without improvement of the signal to noise ratio so that one frequently obtains false and misleading measurements.

Accordingly, it is an important object of the invention to provide cuvettes for liquid chromatographic analysis which will deliver a higher level of signal strength from the fluorescent properties of the samples (compounds) under investigation.

It is a further object of the invention to provide such cuvettes, some of which may be used for the measurement of light transmission through the samples and/or the optical density of the samples.

These and other objects, advantages, features and uses will be apparent during the course of the following discussion when taken together with the accompanying drawing.

Broadly, the invention is directed toward providing a cuvette which is of such construction that the laminar flow is not greatly impaired. This is necessary in order to prevent turbid behavior of the liquid in the vicinity of the walls surrounding the chamber the contents of which are being investigated by optical means.

The measurements are made in a detection area in the form of an elongated chamber which is fed from an inlet orifice. An outlet orifice, out of which the liquid flows from the chamber, is at the end of the chamber opposite the inlet orifice. Since the pressures in the chamber may reach the order of 5,000 to 10,000 psi, it is very important that the measurement chamber be sealed.

To improve the optical efficiency and to maximize the amount of optical energy reaching the photomultiplier or other detector, the measurement chamber is embedded or surrounded by or in intimate contact with a body of clear plastic, glass or quartz, the reflecting surface of which is a surface of revolution formed by a generating curve which is a circle, an ellipse, a parabola or other curve. The reflecting surface will therefore be spherical or aspherical (generated by a curve other than a circle).

To maximize the fluorescent energy detected in the chamber, it is desirable to confine the fluorescing zone to an area which offers no more cross section than the illuminating beam.

In the accompanying drawing, forming a part of this application, in which like numerals are employed to designate like parts throughout the same:

Figure 2:
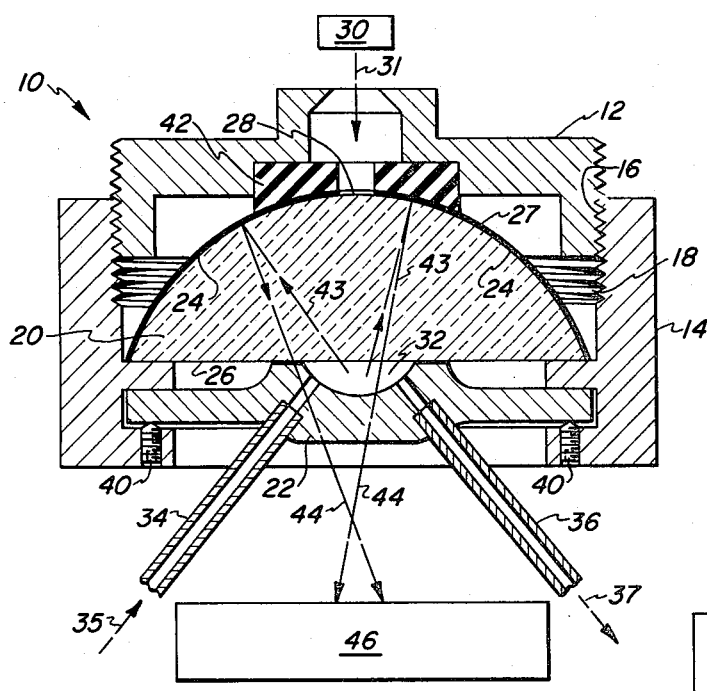
FIG. 2 is a sectional view, taken on lines 2—2 of FIG. 1, viewed in the direction of the arrows.
Figure 1:
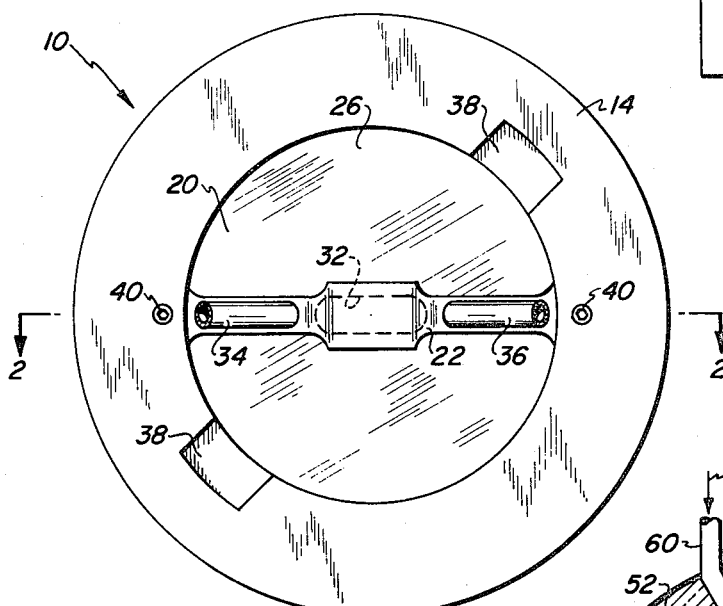
FIG. 1 is a front elevational view of a flow-through cuvette of the invention.

In the drawing, wherein, for the purpose of illustration, there are shown various embodiments of the invention, the numeral 10 designates a cuvette of the invention, generally. Cuvette 10 is seen to comprise (FIGS. 1 and 2) a two element housing 12 and 14 having mating threads 16 and 18, a solid block 20 of optically transparent material such as quartz, glass or clear plastic and a bar 22 of metal or similar material.

Solid block 20 has a curved surface 24 which is a surface of revolution generated by a circle or it is aspherical, namely, generated by a curve other than a circle such as an ellipse or a parabola, and a flat surface 26. Surface 24 is covered by a reflective material 27 such as aluminum except at area 28 which is left open to allow light from a source 30 to be transmitted in the direction of arrow 31 into and through block 20. An elongated optically clear chamber 32 is embedded in bar 22 and is provided with an entrance orifice 34 and an exit orifice 36.

Housing elements 12 and 14 are threaded together by means of threads 16 and 18 and to prevent damage, an elastomeric pad 42 is held securely between housing element 12 and surface 24. Bar 22 is inserted in keyways 38 of element 14 and is rotated to the position of FIG. 1 where it is held in position by means of set screws 40. In this position, the optically open portion of chamber 32 is in intimate contact with flat surface 26.

In operation, light from light source 30 is transmitted and directed through block 20 to enter chamber 32. In chamber 32, the light contacts the liquid which enters through entrance 34 in the direction of arrow 35 and leaves through exit 36 in the direction of arrow 37 and contains the material to be analyzed. The liquid fluoresces and produces a multitude of rays 43, two of which are illustrated. These rays are reflected from surface 24 as shown by rays 44. Rays 44 are collected and received by a photomultiplier 46 or similar instrument such as a photosensor with collector. The source of light 30 and the photomultiplier 46 are shown diagrammatically.

Cuvette 10 may be used in single cuvette systems for absolute measurements or a plurality of them may be used in comparative measuring systems such as have been described in our co-pending application Ser. No.

450,676, filed Mar. 13, 1974, now U.S. Pat. No. 3,985,441, which is owned by the assignee hereof.

Figure 3:
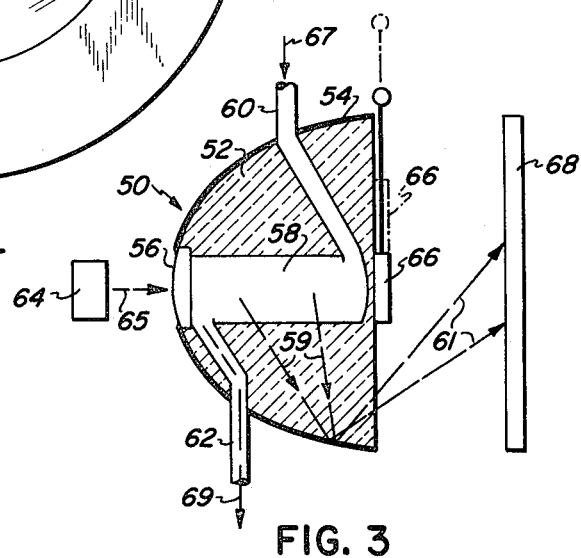
FIG. 3 is a diagrammatic elevational view of a further embodiment of the invention.

In FIG. 3 there is shown a cuvette 50 which comprises a solid block 52 of quartz, clear plastic, glass or similar material of the same configuration as has been described heretofore. Reflective material is coated on curved surface 54 except in the area of a quartz window or lens 56. Embedded in block 52 is an elongated chamber 58 to contain the liquid to be analyzed. The liquid enters chamber 58 through entrance means 60 and leaves through exit means 62 as shown by the adjacent arrows 67 and 69.

Light from a source 64 is directed in the direction of arrow 65 through quartz window or lens 56 into chamber 58. A mask or chopper 66 is provided such that it is movable by means well-known in the art between the positions shown in the solid and dashed lines in FIG. 3. In the solid line position, the fluorescing rays 59 (two of which are shown) are reflected as indicated by 61 to a photodetector or photomultiplier 68. In the dashed line position, the light is transmitted through the liquid to enable one to make transmissivity or optical density measurements. Cuvette 50 may also be used for single or multiple system measurements.

Figure 4:
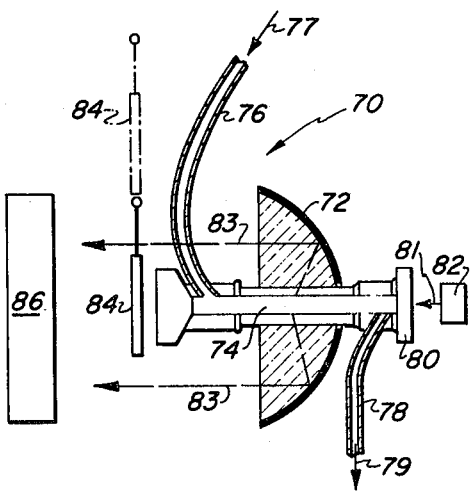
FIG. 4 is a view similar to that of FIG. 3 of a still further embodiment of the invention.

In FIG. 4, there is illustrated a further cuvette 70 of the invention. Cuvette 70 is seen to comprise a solid block 72 similar to that described heretofore, an elongated chamber 74 having entrance means 76 and exit means 78. Liquid enters in the direction of arrow 77 and exits in the direction of arrow 79. A quartz window 80 directs the light which it receives in direction of arrow 81 from a light source 82 into chamber 74 to impinge on the liquid therein. A mask 84 is movable between two positions. In the solid line position rays 83 (two of which are shown) are directed toward photodetector 86 for fluorescent measurements. In the dashed line position, the light from source 82 goes through chamber 74 to detector 86 for the measurement of the transmissivity or the optical density of the liquid in the chamber. If desired, block 72 may be a hollow body with a reflector as its curved surface.

Cuvette 70 may also be used for direct measurement in single systems or in the multiple unit systems described in the aforementioned patent application.

Figure 5:
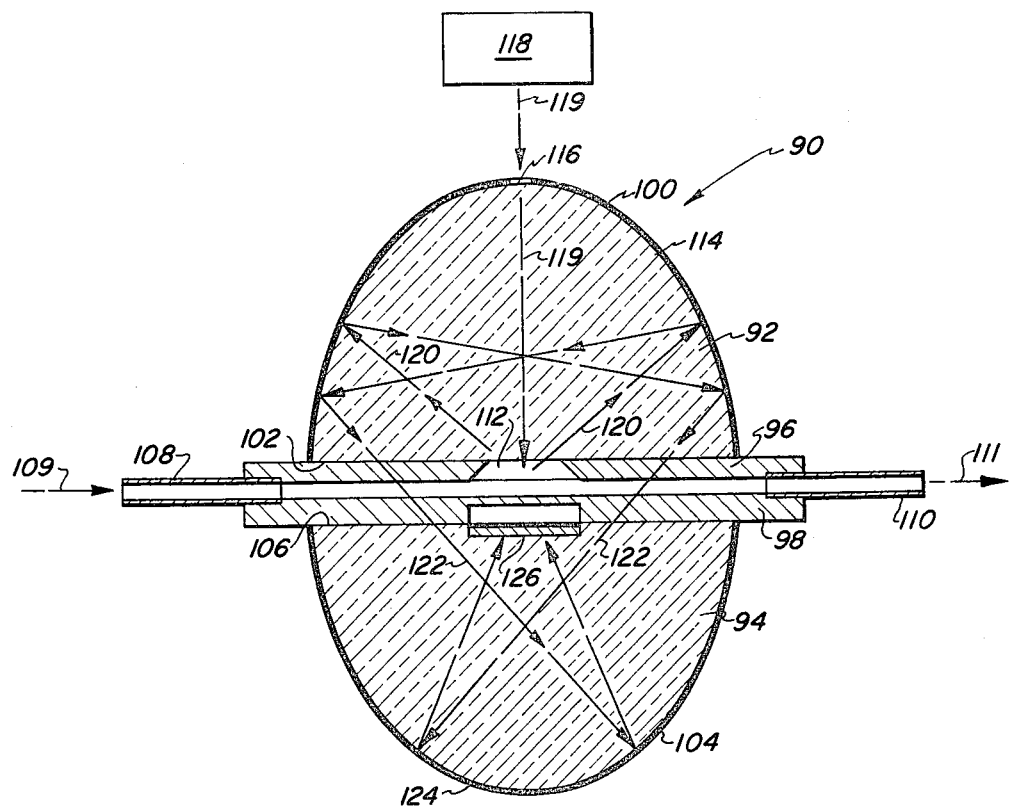
FIG. 5 is a view, similar to that of FIG. 2, of a further embodiment of the invention.

In FIG. 5 there is illustrated a cuvette 90 of the invention. It comprises a pair of spaced apart optically clear, solid blocks 92 and 94 which are joined by a housing formed of mating bars 96 and 98 (details not shown). Solid blocks 92 and 94 are solids of revolution which are generated by curves such as circles, ellipses or parabolas and are formed having a curved surface and a flat surface. The curved surface of block 92 is designated as 100 and the flat surface as 102. The curved surface of solid block 94 is designated as 104 and the flat surface as 106.

In FIG. 5, the curved surfaces 100 and 104 are portions of ellipsoids but they may be portions of spheres, paraboloids or other surfaces or revolution. The fluid to be studied enters through entrance 108 in the direction of arrow 109 and leaves through exit 110 in the direction of arrow 111. An elongated, optically clear chamber 112 is embedded in bar 96 such that a portion of the chamber is in contact with flat surface 102 of block 92. The surface 100 is covered with reflective material such as aluminum except that an opening 116 is left in the reflective coating 114.

Light from a light source 118 is directed toward chamber 112 in the direction of arrows 119. The light entering the chamber 112 excites the fluid therein to fluoresce and rays are emitted therefrom (two rays 120 are shown). These rays are reflected in block 92 by reflector 114 until they enter block 94 as rays 122. The curved surface 104 of block 94 is covered with a reflective material 124 such as aluminum and the rays 122 are directed so they impinge on a photosensitive detector or photomultiplier 126. Any suitable detector may be used. The electrical connections to the detector 126 and the electronic system used in connection therewith are not shown.

It is apparent to those skilled in the art that the elongated, optically clear chambers may take any shape so long as there is sufficient liquid therein to produce usable light signals for transmission to the detector.

While various embodiments of the invention have been shown and described, it is apparent to those skilled in the art that modifications are possible without departing from the spirit of the invention or the scope of the subjoined claims.

The embodiments of the invention in which an exclusive property or privilege is claimed are defined as follows:

1. A cuvette for liquid chromatographic analysis wherein light from a light source is directed to a sample of a liquid in the cuvette and a maximum amount of light scattered by the liquid is collected from said cuvette comprising:

an optically clear chamber adapted to contain therein the sample of the liquid and disposed to receive light from the light source;

entrance means and exit means connected to the chamber to permit the liquid to flow therethrough;

a solid block of light transparent material in the shape of a solid of revolution having a curved light directing surface generated by a curve having a configuration and placement relative to the chamber such that said maximum amount of light scattered by the liquid in the chamber is collected and directed in a specific direction; and a reflective material on the light directing surface of the solid block for reflecting essentially all of the light at that surface to maximize the amount of optical energy directed in the specific direction.

2. The cuvette of claim 1 wherein:
the chamber is elongated and its axis is in alignment with the light from the light source.

3. The cuvette of claim 2 including:
a mask at the end of the elongated chamber opposite the end at which the light from the light source enters the elongated chamber.

4. The cuvette of claim 1 wherein:
the chamber is elongated;
the light directing surface of the solid block of transparent material is spaced from the optically clear chamber and the solid block has a flat surface which is adjacent the optically clear chamber;
the reflective material is a coating on the outer curved light directing surface of said block, said reflective coating having an opening therein to permit the light from the light source to pass therethrough and impinge on the liquid in the optically clear chamber.

5. The cuvette of claim 4 including:
holding means for holding the flat surface of the optical body in intimate contact with the outer surface of the elongated chamber.

6. The cuvette of claim 5 wherein the holding means comprises:
- a housing having two elements having mating threads;
- a resilient pad surrounding the opening in the reflective coating;
- a bar, the elongated optically clear chamber being embedded in the bar so that a portion of its surface is exposed;
- the mating threads being engaged such that the resilient pad is in contact with one element of the housing and the curved surface of the solid body and the other element of the housing is in contact with the flat surface of the solid block;
- the other element of the housing having opposed keyways therein to receive the ends of the bar;
- the bar being rotated into position wherein it is out of alignment with the keyways;
- holding means for holding the bar in this out of alignment position such that the elongated optically clear chamber is in contact with the flat side of the solid block.

7. The cuvette of claim 1 wherein:
the optically clear chamber is partially embedded in the solid block with its axis in a radial direction with respect to the block.

8. The cuvette of claim 7 including:
a quartz window adjacent one end of the optically clear chamber to direct the light from the light source therein.

9. The cuvette of claim 8 including:
a shutter at the end of the optically clear chamber opposite the quartz window movable between a first position wherein the light entering the chamber passes therethrough and a second position wherein the light entering the chamber is precluded from passing therethrough and is reflected by the reflective material.

10. The cuvette of claim 7 wherein:
the optically clear chamber is completely embedded in the solid block.

11. The cuvette of claim 10 including:
a quartz window adjacent one end of the optically clear chamber to direct the light from the light source therein.

12. The cuvette of claim 11 including:
a shutter at the end of the optically clear chamber opposite the quartz window movable between a first position wherein the light entering the chamber passes therethrough and a second position wherein the light entering the chamber is precluded from passing therethrough and is reflected by the reflective material.

13. The invention of claim 1 including:
- a second solid block of light transparent material having a curved surface generated by a curve;
- both solid blocks of light transparent materials having reflective material on at least a portion of their curved surfaces;
- the solid blocks having flat surfaces placed in juxtaposition;
- a pair of mating sections placed to hold the said flat surfaces in position;
- the chamber being embedded in one of said mating sections;
- a photodetector mounted in the other mating section;
- the blocks being positioned such that light from the light source excites the contents of the chamber which contents fluoresce and the said fluorescent light is directed by the reflective material on both solid blocks to the photodetector.

* * * * *